(12) United States Patent
Shore et al.

(10) Patent No.: US 6,821,383 B2
(45) Date of Patent: Nov. 23, 2004

(54) PREPARATION OF MODIFIED FLUFF PULP, FLUFF PULP PRODUCTS AND USE THEREOF

(75) Inventors: Michele Merrette Shore, Bridgewater, NJ (US); A. Levent Cimecioglu, Princeton, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 10/058,723

(22) Filed: Jan. 28, 2002

(65) Prior Publication Data

US 2003/0024661 A1 Feb. 6, 2003

Related U.S. Application Data

(60) Provisional application No. 60/279,277, filed on Mar. 28, 2001, and provisional application No. 60/303,498, filed on Jul. 6, 2001.

(51) Int. Cl.[7] .......................... D21H 9/00; D21H 23/00; D06M 13/322; D06M 13/35
(52) U.S. Cl. .......................... 162/9; 162/157.6; 162/72; 8/181; 8/120; 536/56
(58) Field of Search ..................... 162/9, 157.6, 158, 162/168.1–168.3, 164.1, 157.1, 72; 8/120, 116.1, 116.4, 181–185, 108.1, 115.51; 604/375–378; 536/36, 56

(56) References Cited

U.S. PATENT DOCUMENTS

| 3,868,955 | A | 3/1975 | Steiger et al. ............... 128/296 |
| 3,987,968 | A | 10/1976 | Moore et al. ................ 241/28 |
| 4,822,453 | A | 4/1989 | Dean et al. ............... 162/157.6 |
| 5,698,688 | A | 12/1997 | Smith et al. .................. 536/56 |
| 6,031,101 | A | 2/2000 | Devine et al. .............. 546/112 |
| 6,176,973 | B1 | 1/2001 | Norlander ................ 162/157.6 |
| 6,228,126 | B1 * | 5/2001 | Cimecioglu et al. ......... 8/108.1 |
| 6,254,724 | B1 * | 7/2001 | Seltzer et al. .................. 162/70 |
| 6,319,361 | B1 * | 11/2001 | Smith et al. ................ 162/146 |
| 6,331,619 | B1 * | 12/2001 | Besemer et al. ............ 536/105 |
| 6,379,494 | B1 * | 4/2002 | Jewell et al. ................... 162/9 |
| 6,409,881 | B1 * | 6/2002 | Jaschinski ....................... 162/9 |
| 6,524,348 | B1 * | 2/2003 | Jewell et al. ................ 8/116.1 |
| 6,540,876 | B1 | 4/2003 | Cimecioglu et al. ........ 162/177 |
| 2002/0026993 | A1 * | 3/2002 | Thornton et al. ........... 162/175 |
| 2002/0072598 | A1 * | 6/2002 | Besemer et al. .............. 536/56 |
| 2002/0098317 | A1 * | 7/2002 | Jaschinski et al. ............ 428/72 |
| 2003/0024661 | A1 * | 2/2003 | Shore et al. .................... 162/9 |
| 2003/0078556 | A1 * | 4/2003 | Sasaki et al. .......... 604/385.25 |

FOREIGN PATENT DOCUMENTS

| EP | 1 077 285 A1 | 2/2001 | .......... D21H/11/20 |
| WO | WO 99/23117 | 5/1999 | .......... C08B/15/04 |

OTHER PUBLICATIONS

Kitaoka T. et al: "Chemical Modification of Pulp Fibers by Tempo–Mediated Oxidation", Nordic Pulp and Paper Research Journal, Stockholm, SE, vol. 14, NR.4, pp. 279–284.

* cited by examiner

*Primary Examiner*—José A. Fortuna
(74) *Attorney, Agent, or Firm*—David P. LeCroy

(57) ABSTRACT

This invention relates to a method of producing modified fluff pulp comprising treating cellulose pulp with a nitroxide-mediated oxidation method and fluffing the treated cellulose pulp. The invention further relates to the modified fluff pulp prepared therefrom and absorbent articles comprising the modified fluff pulp.

26 Claims, 2 Drawing Sheets

PREPARATION OF MODIFIED FLUFF PULP, FLUFF PULP PRODUCTS AND USE THEREOF

This invention claims priority from provisional applications 60/279,277 and 60/303,498 filed Mar. 28, 2001 and Jul. 6, 2001, respectively.

FIELD OF THE INVENTION

This invention relates to a method of producing modified fluff pulp comprising treating cellulose pulp with a nitroxide-mediated oxidation method and fluffing the treated cellulose pulp. The invention further relates to the modified fluff pulp prepared therefrom and absorbent articles comprising the modified fluff pulp.

BACKGROUND OF THE INVENTION

Cellulose products such as absorbent pads and other structures are composed of fluffed cellulose fibers, which, in turn, are primarily composed of individual cellulose chains. Commonly, cellulose fibers are crosslinked to impart advantageous properties such as increased absorbent capacity, bulk, and resilience to products containing such crosslinked fibers.

Crosslinked cellulose fibers and methods for their preparation are widely known. See, for example, Tersoro and Willard, Cellulose and Cellulose Derivatives, Bikales and Segal, eds., Part V, Wiley-Interscience, New York, (1971), pp. 835–875. Crosslinked cellulose fibers are prepared by treating fibers with a crosslinking agent. Crosslinking agents are generally bifunctional compounds that, in the context of cellulose crosslinking, covalently couple a hydroxyl group of one cellulose chain to another hydroxyl group on a neighboring cellulose chain. Despite washing the fiber after the crosslinking process, residual amounts of these often expensive crosslinking agents remain in the fiber. Crosslinking agents are known to irritate the skin and require extra production steps in order to remove and dispose of the offending chemicals, particularly in applications where articles composed of these fibers are used directly on the skin. Such processes are often complex and not commercially viable.

However, in general, absorbent articles comprising fluffed crosslinked fibers have greater absorbent capacity, bulk, and resilience than fluffed noncrosslinked or untreated cellulose fibers. Additionally, excessive crosslinking can produce brittle fibers of excessive stiffness, thereby making them difficult to form into densified sheets for transport and to subsequently fluff without fiber damage. Further, when compressed in a dry state, these fibers generally exhibit low responsiveness to wetting. That is, once compressed in a dry state, pads of conventionally crosslinked fluff pulp do not regain substantial amounts of their prior absorbent capacity upon wetting, and may lose their ability to "wick" as defined by the ability to rapidly transfer fluid away from the point of insult.

Conversely, absorbent articles, such as pads made from unmodified cellulose fibers, are often excessively flexible, and may lose their structural integrity in the wet state by collapsing. While suitable for some applications requiring a higher density pad, such absorbent articles have low resilience and are characterized by lower overall absorbent properties, particularly under high moisture conditions.

Further, such articles are often unable to maintain their "wicking" ability when moistened, as the pad collapses and separates when compressed, thus interfering with the ability of the pad to transfer moisture. The inability to maintain wicking tends to negatively impact the fluid storage capacity of the absorbent article, leads to leaking of the liquid from the article and subsequent irritation of the wearer's skin. Attempts to increase the absorption of such articles by the incorporation of superabsorbent polymers (particularly hydrogel-forming polymeric materials) may also have an adverse effect on wicking at certain concentrations. This is due to a phenomenon known as "gel-blocking" where the expanding superabsorbent polymer gel blocks the open pores within the article and prevents the transfer of fluid to the outer parts of the article.

Attempts to improve the fluid transport properties of absorbent articles have been reported in the literature. Fluid transport properties are defined to be the amount of fluid that can be wicked or transported throughout an article and may be measured by a combination of wicking rate and wicking capacity. Attempts to improve fluid transport properties include the densification of the absorbent article or the addition of high surface area fibers or particles to the article with the intent of increasing the wicking rate. Although these methods effectively create smaller pore sizes in the absorbent article thereby improving wicking rate, they also tend to reduce the wicking capacity of the article having an undesirable impact on the overall fluid transport properties.

Accordingly, there remains a need for a facile process of producing a modified fluffed cellulose pulp having improved absorption properties including absorption capacity, structural integrity, wicking rate and wicking capacity that may be used in absorbent articles.

SUMMARY OF THE INVENTION

Figure 1:
FIG. 1 is a photo micrograph of an unmodified cellulose pulp fiber which indicates that the fiber has a small degree of curl.

A facile process for obtaining a modified cellulose fluffed pulp has now been discovered which does not require the use of any crosslinking agents.

The method of preparing modified fluffed pulp comprises a) treating cellulose pulp with a nitroxide-mediated oxidation method; and b) fluffing the treated fibers whereby the modified fluffed pulp contains from about 1 to about 50 mmole of aldehyde/100 g of cellulose pulp.

The modified fluffed pulp prepared according to this method is characterized by highly absorbent properties including absorption capacity, structural integrity, wicking rate and wicking capacity.

The absorbent articles comprising the modified fluff pulp of the present invention provide a variety of substantial performance advantages and are useful in a variety of absorbent products including, but not limited to, adult incontinence products, (disposable) diapers, sanitary napkins, tampons, and bandages.

DETAILED DESCRIPTION OF THE INVENTION

A facile process of producing a modified fluffed cellulose pulp has now been discovered which eliminates the need for crosslinking agents. The method of preparing modified fluffed pulp comprises a) treating cellulose pulp with a nitroxide-mediated oxidation method; and b) fluffing the treated fibers.

The modified fluffed pulp prepared via this process is characterized by an aldehyde content of between about 1 to about 50 mmole/100 g cellulose. The aldehyde functionality generated on the cellulose of this invention, by virtue of their reactivity with hydroxyl groups on neighboring cellulose chains, in effect enable "self-crosslinking" interactions either within (intra-fiber) the cellulose fiber or between neighboring (inter-fiber) cellulose fibers.

These self-crosslinking cellulose pulp fibers are obtained via oxidation of cellulose pulp in an aqueous media with an oxidant having an equivalent oxidizing power of up to 15.0 g of active chlorine per 100 g of cellulose and an effective mediating amount of nitroxyl radical, the reaction being carried out at a pH of about 3.0 to about 10.5 and a temperature of from about 5 to about 50° C. In particular, the primary ("C-6") alcohols on the cellulose pulp are selectively oxidized. The nitroxyl radical mediator used herein is a di-tertiary alkyl nitroxyl radical having one of the following formulas:

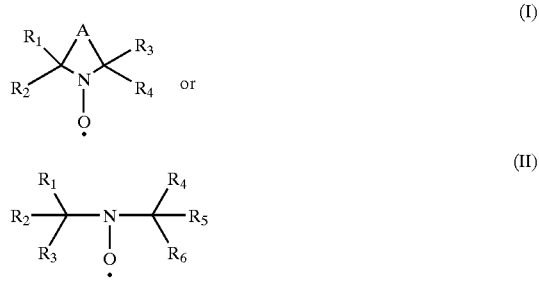

where A represents a chain of preferably two or three atoms (saturated or unsaturated), in particular carbon atoms or a combination of one or two carbon atoms with an oxygen or nitrogen atom, and the $R_1$–$R_6$ groups represent the same or different alkyl groups. Chain A may be substituted by one or more groups such as alkyl, alkoxy, aryl, aryloxy, amino, amido or oxo groups, or by a divalent group or multivalent group which is bound to one or more other groups having formula 1. Particularly useful nitroxyl radicals are di-tertiary alkyl nitroxyl radicals having the formula:

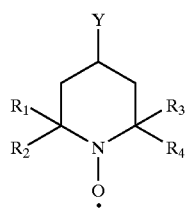

where Y is either H, OH, OR', NH—C(O)—R', OC(O)R', keto or acetal derivatives, thereof, wherein R' is alkyl or aryl. Each of the $R_1$–$R_4$ groups represent the same or different alkyl groups of 1 to 18 carbon atom and more particularly methyl groups. Nitroxyl radicals of this type include those where a) the $R_1$–$R_4$ groups are all methyl and Y is H, i.e., 2,2,6,6-tetramethyl-1-piperdinyloxy (TEMPO); b) $R_1$–$R_4$ groups are methyl and X is OH and identified as 4-hydroxy TEMPO; and c) $R_1$–$R_4$ groups are methyl and Y is NH—C(O)—$CH_3$ and identified as 4-acetamido-TEMPO. The preferred nitroxyl radical is TEMPO or 4-acetamido-TEMPO. The nitroxyl radical is used in an effective amount to mediate the oxidation and more particularly from about 0.001 to about 20%, even more particularly from about 0.005 to about 5% by weight, and even more particularly from about 0.01 to 0.1%, all percents are by weight based on the weight of cellulose pulp. The nitroxyl radical can be added to the reaction mixture or generated in situ from the corresponding hydroxylamine or oxoammonium ion. Nitroxyl radical mediators contemplated may include, for example, nitroxyl radicals obtained from precursors such as hydroxy benzotriazole.

The oxidant used in this invention can be any material capable of converting nitroxyl radicals to their corresponding oxoammonium salts. Particularly useful oxidants are the alkali or alkaline-earth metal hypohalite salts such as sodium hypochlorite, lithium hypochlorite, potassium hypochlorite or calcium hypochlorite. An alkali or alkaline earth-metal hypobromite salt may also be used and it may be added in the form of the hypobromite salt itself, such as sodium hypobromite, or it may be formed in situ from the addition of a suitable oxidant such as sodium hypochlorite and an alkali or alkaline-earth metal bromide salt such as sodium bromide. The bromide ion is generally in the form of sodium bromide. Additional oxidants that can be used in this method include hydrogen peroxide in combination with a transition metal catalyst such as methyltrioxorhenium (VII); hydrogen peroxide in combination with an enzyme; oxygen in combination with a transition metal catalyst; oxygen in combination with an enzyme; peroxyacids such as peracetic acid and 3-chloroperoxybenzoic acid; alkali or alkaline-earth metal salts of persulfates such as potassium persulfate and sodium persulfate; alkali or alkaline-earth metal salts of peroxymonosulfates such as potassium peroxymonosulfate; chloramines such as 1,3,5-trichloro-1,3,5-triazine-2,4,6(1 H,3H,5H)trione, 1,3-dichloro-1,3,5-triazine-2,4,6(1 H,3H, 5H)triione sodium salt, 1,3-dichloro-5,5-dimethylhydrantoin, 1-bromo-3-chloro-5,5-dimethylhydrantoin, and 1-chloro-2,5-pyrrolidinedione; and alkali or alkaline-earth metal salts of ferricyanide. This list of oxidants is only illustrative and is not intended to be exhaustive. The oxidants can be used alone or in combination with an alkali or alkaline-earth metal bromide salt. The preferred oxidant is sodium hypochlorite or sodium hypobromite formed from the addition of sodium hypochlorite and sodium bromide.

The important factor in the use of the oxidant is that it must be used in a limited amount so that the oxidant has the equivalent oxidizing power of from about 0.05 g to about 15.0 g of active chlorine per 100 g of cellulose pulp. Also suitable amounts of oxidant used will have an equivalent oxidizing power of from about 0.5 g to 10 g of active chlorine, from about 0.5 g to about 5 g of active chlorine and from about 0.5 g to about 2.5 g of active chlorine, all values based on 100 g of cellulose pulp. When sodium hypochlorite is used, it is used in a limited amount of up to about 30 percent by weight based on the weight of cellulose pulp. Also suitable are amounts of sodium hypochlorite ranging from about 0.05% to about 20%, from about 1% to about 10% and from about 1% to about 5% by weight, all values based on the weight of cellulose pulp. Bromide in the form of sodium bromide will generally be used in an amount of up to 5% by weight and preferably from about 0.1 to 2% by weight based on the weight of cellulose pulp.

A co-catalyst can also be used to increase the rate and/or selectivity of the nitroxide mediated oxidation process. Particularly suitable co-catalysts are described in U.S. Pat.

No. 6,540,876, the disclosure of which is incorporated herein by reference. The co-catalyst is generally present in a catalyst-effective amount, particularly in an amount of about 0.005 to 5.0%, more particularly in an amount of about 0.01 to 0.5%, most particularly in an amount of about 0.01 to 0.20 by weight based on the weight of the cellulose pulp.

The cellulose material used as the starting material may be any cellulose pulp material. This includes hardwood or softwood cellulosic fibers such as bleached and unbleached sulfate (Kraft), bleached and unbleached sulfite, bleached and unbleached soda, neutral sulfite, semi-chemical, groundwood, chemi-groundwood, and any combination of these fibers. In addition, cotton, cotton linter and regenerated cellulose fibers including regenerated viscose, rayon or lyocell can also be used, as well as recycled waste papers from various sources. Dry lap or never dried pulps maybe used. Preferred fibers in fluff pulp applications are generally long softwood fibers such as pine, douglas fir, spruce, etc. The consistency in water of the cellulose or pulp that is used will be from about 0.1 to 15% by weight solids in water and preferably from about 1 to 5% by weight.

The oxidation reaction of the cellulosic material is preferably carried out in an aqueous media. The pH of the reaction is maintained at a pH between about 3.0 to about 10.5. Also suitable reaction pHs range from between about 4.0 to 9.5, and from about 7.0 to about 9.5. The temperature is maintained at a temperature in the range of from about 5° C. to about 50° C. Also suitable reaction temperatures are in the range of from about 20° C. to about 40° C. The extent of the reaction is controlled by the amount of oxidant used or the reaction time. Generally the reaction time will be from about 1 minute to about 5 hours. Also suitable reaction times range from about 5 minutes to about 60 minutes, and from about 10 minutes to about 30 minutes.

By using the reagent and component amounts as defined previously and the noted reaction conditions, controlled amounts of aldehyde functionality, particularly C-6 aldehyde, can be obtained. The cellulose aldehyde derivatives prepared in accordance with this invention will have effective aldehyde functionality of from about 1 mmole to 50 mmoles of aldehyde/100 g of cellulose pulp. Also suitable ranges of effective aldehyde content range from about 1 mmole to about 20 mmole, from about 1 mmole to about 10 mmole and from about 1 mmole to about 6 mmole; all aldehyde content values based on 100 g of cellulose pulp. Carboxylic acid functionality will also be generated or formed during the oxidation process. Amounts of carboxyl content generated may be up to 100 mmole/100 g of cellulose pulp. It should be noted that this amount of carboxylic acid functionality is in addition to what may already be present in the cellulose pulp naturally or by virtue of the type of processed pulp used, such as bleached sulfate and bleached sulfite.

The effective level of aldehyde is an important aspect of this invention and one way this can be defined is by the ratio of aldehyde to generated carboxylic acid functionalities. Such levels can be defined by aldehyde to generated carboxylic acid ratios of greater than or equal to 0.2 (based on mmole/100 g of cellulose or cellulose pulp of each functionality). The significance of the combination of aldehyde and carboxylic acid content is manifested in the crosslinking of the fibers of the oxidized cellulose pulp. It is thought that the desirable properties of the fibers are due to crosslinking occurring through the hemi-acetal and/or acetal bond formation of the generated aldehydes and adjacent hydroxyl containing chains.

Generally, after oxidation, the cellulosic fibers should be dewatered, dried and directly formed into a pulp sheets or rolls. This sheet can be either compacted and densified for shipment, or made to a low density for direct use as an absorbent article or to aid in subsequent defibration for use as an absorbent article. "Fluffing" or mechanical defibration may be accomplished by a variety of means known in the art, for example using a hammermill, at any step after the dewatering or drying steps. "Fluffing" processes are known in the art and are described, for example, in U.S. Pat. No 3,987,968, issued to D. R. Moore and O. A. Shields on Oct. 26, 1976, the disclosure of which in incorporated herein by reference. The resultant fluff pulp can then be dry or air laid into absorbent structures by techniques known in the art.

The modified fluff pulp of the present invention has a high degree of structural integrity. Structural integrity refers to the ability of the fluff pulp to maintain its shape. The structural integrity of the absorbent articles comprising the fluff pulp of the present invention is determined by a variety of factors including fiber strength, stiffness, and resiliency.

Figure 2:
FIG. 2 is a photo micrograph of an aldehyde and carboxyl group modified fiber prepared according to the present invention (See Example 1, infra) which indicates that the fiber has greater degree of curl than the corresponding unmodified cellulose pulp fiber of FIG. 1.

Resiliency is herein defined as the ability of an absorbent product to recover or "spring back" after compression under forces and pressures of common use, thus maintaining the absorbent article's structural integrity. A combination of factors impacts the resilience of absorbent articles. It has been noted that the tendency of a fiber to curl contributes to the resiliency and thus structural integrity of absorbent articles comprising the fiber. Accordingly, it is thought that the increased structural integrity of the fluff pulp of the present invention is due to the increased tendency of the oxidized fibers to "curl" compared to the corresponding unmodified fibers, as illustrated by the photo micrographs of the unmodified cellulose fiber in FIG. 1 and the corresponding oxidized fiber in FIG. 2.

The modified fluff pulp of the present invention and articles comprising the fluff pulp demonstrate increased water/saline absorbency even under high load (for example at 250 psi, see Example 3, infra) and show an increased ability to wick as compared to the corresponding unmodified fluff pulp. Absorbent capacity, as defined herein, is the total weight fluid absorbed per weight fluff pulp.

Additionally, in contrast to known unmodified and conventionally crosslinked fluffed pulps, the modified fluff pulp of the present invention has improved fluid transport properties characterized by a surprising simultaneous improvement in wicking rate and wicking capacity. Wicking capacity is defined herein as the amount of liquid that is being wicked or transported throughout the article per unit time. Wicking rate is defined herein as the distance the fluid moves through the article per unit time. Accordingly, the modified fluff pulp prepared by the present process may be used in absorbent articles to improve a combination of desirable properties as compared to the corresponding unmodified fluff pulp, namely, absorbent properties as demonstrated by absorbent capacity, structural integrity, wicking rate and wicking capacity.

Further, in order to increase the absorbency of a product, absorbent articles are often treated with super absorbent polymers ("SAPs") to enhance the absorbency of the article into which they are incorporated. SAPs are well known in the art and described, for example, in U.S. Pat. No. 4,822, 453, the disclosure of which is incorporated herein by reference. SAPs, particularly those prepared of substantially water-insoluble hydrogel-forming materials, tend to adversely affect the transfer of liquid (or wicking) throughout the absorbent article due to gel-blocking effects. It is expected that the superior wicking ability and capacity of the modified fluff pulp of the present invention may be particularly advantageous when it is necessary to treat an absorbent article comprising such pulp with a SAP. Moreover, the improved absorbent capacity of the modified fluff pulp may enable a reduction in the use of expensive SAP as well as advantageously reducing the SAP chemical load on the environment, a particularly important factor in the disposal of the absorbent articles.

Due to the oxidative modification of the present invention, the modified fluff pulp has a relatively high level of anionic groups which may enable the improved retention of conventional complementary additives such as debonders, fixatives and chemical additive binders. Also the modified fluffed pulp of the present invention may also be used to improve typical "fluffed" products in which odor reduction is desirable as it is known that polysaccharide aldehydes interact with aldehyde-reactive functionality thereby reducing the odor caused by compounds containing ammonia, amine and sulfur functionalities. See U.S. Pat. No. 3,868,955 filed Oct. 5, 1973.

In addition to the modified fluffed pulp of the present invention, the absorbent articles described herein may include conventional fluffed fibers, refined fibers, mechanically-treated fibers, synthetic fibers, modified fibers or any combination or blend thereof. Such fibers may be crosslinked and air or wet laid.

Such articles include, without limit, diapers (disposable, training pants, all suitable for adult and child products), and feminine care and/or hygiene products (including sanitary napkins, tampons, liners, etc.), medical or surgical dressings (including bandages, wipes, sponges, drapes, clothing, bed pads, etc.) food (including meat) packaging pads, liners or casings, humidity or odor removing filters, insulation (against moisture, heat or acoustic problems), agricultural materials needing to retain moisture and tissue and towel applications including, without limit, tissue and towels, including cleaning wipes, paper handkerchiefs, cosmetic wipes, napkin/serviettes, etc.

The following examples will more fully illustrate the embodiments of this invention. In the examples, all parts and percentages are by weight and all temperatures in degrees Celsius unless otherwise noted. Also, unless otherwise noted, when referring to the pulp by weight, it is the weight of the pulp per se, i.e., it includes equilibrium moisture content.

EXAMPLES

Procedures

Preparation of Air Laid Pads

Modified and unmodified pulps at 3% consistency were adjusted to the desired pH level of 3.6 or 8.0, using dilute $H_2SO_4$ or NaOH, respectively. Handsheets were made on a sheet former (M/K model, available from M/K Systems, Pennsylvania, U.S.A.) at a weight of 161 $g/m^2$. The handsheets were couched but not pressed, and dried in a drum dryer at 138° C. The resulting sheets were allowed to equilibrate under ambient conditions prior to defibration and screening in a Mikro-Bantam laboratory hammermill (Micron Powder Systems, Model CF, 1725 rpm, 1 cm screen size). The fluff fibers were then allowed to equilibrate under ambient conditions and their moisture content was recorded.

Fiber (6.40 g) was dispersed in air and formed into 3 equal weight layers using a small mixer. The layers were then pressed together for one minute using a hydraulic press to obtain a density of 0.15 $g/cm^3$. The resultant pad was trimmed to a circular area of 63.62 $cm^2$ and a weight of 650 $g/m^2$. The pad was then re-pressed for 1 minute, and allowed to recover for 1 minute before measuring the final thickness with a no load caliper. All pads were pressed to obtain an equal density of 0.15 $g/cm^3$, which is typically found in baby diapers.

Absorbent Capacity

The total absorbent capacity of air laid pads was measured using a Gravimetric Absorbency Test System ("GATS") from M/K Systems. Pads (63.62 $cm^2$) with a weight of 650 $g/m^2$ and a density of 0.15 $g/cm^3$ were placed on a saturated porous plate (porosity 25–50 $\mu$m) of the same area connected to a reservoir containing the desired testing liquid. A cover was placed above the pads to prevent evaporation effects. The liquid absorbed by the sample was measured by a balance underneath the reservoir during a time interval of 999 seconds and recorded. The total absorbent capacity was calculated as the grams of liquid absorbed per grams of sample at 999 seconds. For the absorbent capacity of pads containing superabsorbent polymers ("SAP"), a 9 cm GF/A glass filter paper is added to the porous plate and pre-saturated prior to contact with the sample pad.

Absorbency Under Load

The total absorbent capacity was also determined for air laid pads under loads commonly experienced in baby diapers. Similar to the procedure described above for absorbent capacity with the GATS, Absorbency Under Load ("AUL") was determined by placing a 0.30 psi load (20,679 dynes/$cm^2$) on the sample. The AUL was calculated as the grams of liquid absorbed per gram of sample under load at 300 seconds. For absorbent pads containing SAP, the AUL was determined at 999 seconds.

Wicking Rate and wicking capacity Measurement

Wicking rate of air laid pads was measured on 7.8 cm×7.8 cm square pads weighing 4.0 g with a density of 0.15 $g/cm^3$. Blue-dyed testing liquid (250 mL) was placed in a trough so that the height of the liquid level in the trough was 1 cm. The sample was then clamped vertically, a wired clamp was placed 1 cm from the bottom of the pad and a second wired clamp was placed exactly 7 cm from the bottom of the pad. Both clamps were connected to an automatic timer. The sample was lowered to the bottom of the trough and the timer was started. The timer was stopped when the liquid level reached the second clamp. The wicking rate in cm/sec was then calculated from the time required for the liquid to travel 6 cm.

Wicking capacity is the volume of liquid absorbed at the time when the liquid has vertically traveled the standard distance of 6 cm for a given pad cross section. All pads are of equal weight and density Dry Resiliency The dry resiliency of air laid pads is defined as the ability of pads to recover or "spring back" after compression under a load. This illustrates the ability of the pad to maintain shape and resiliency under pressure in the dry state. A circular dry pad (63.62 $cm^2$) weighing 4.16 g was compressed in a hydraulic press at an applied pressure of 157 psi ($10.8 \times 10^6$ dynes/$cm^2$) or 250 psi ($17.2 \times 10^6$ dynes/$cm^2$) for 1 minute. The pad was inverted and pressed again for 30 seconds. The pad was removed from the press and allowed to recover for 1 minute, after which the thickness of the pad was determined using a no load caliper and multiple measurements. Dry resiliency is recorded as the average resulting thickness in mm.

Synthetic Urine

"Saline" is hereafter designated by a solution of deionized water containing 0.9% NaCl by weight. A "synthetic urine" was composed to incorporate more of the dissolved components normally found in baby urine. Synthetic urine was made by adding 82.4 g of NaCl, 3.2 g of $CaCl_2 2H_2O$, 4.8 g of $MgSO_4 7H_2O$, 86 g of urea, and 1 g of Pluronic® 10R8 to deionized water for a total volume of 10 liters. Similar to the "saline" solution, the salt concentration was 0.9% by weight of the total solution.

Superabsorbent Polymer is hereafter referred to as SAP, and defiberized fibers after hammermilling are hereafter referred to as "fluff".

EXAMPLE 1

Modification of Pulp Fiber:

a. 4-Acetamido-TEMPO (24.8 mg) and sodium bromide (1.24 g) were added to an 8000 g stirred suspension of bleached softwood kraft pulp at 3% consistency (248 g pulp) and the pH of the mixture was adjusted to 9.5 with 0.98N sodium hydroxide. Sodium hypochlorite (52.2 g of 9.5% solution at pH 9.5) was then introduced all at once and the mixture was stirred at 25° C. for 30 minutes. The pH of the suspension was maintained at 9.5 with 0.98 N NaOH throughout the reaction using a Brinkmann pH STAT 718 Titrino. At the end of the treatment period, the reaction was terminated using either ascorbic acid (ca. 5 g) or ethanol (50 mL) to scavenge the residual hypochlorite.

The pulp was filtered and washed extensively with water at pH 4–5. It was then either re-slurried in water for subsequent use or dried in air at room temperature for future use.

Aldehyde content of the modified pulp was determined by titration of the hydrochloric acid generated during oxime derivatization with hydroxylamine hydrochloride according to the following scheme and procedure.

$$RCHO + NH_2OH \cdot HCl \rightarrow RCHNOH + HCl$$

A suspension of oxidized pulp in water (ca. 200 g at 1% consistency) was adjusted to pH 4 with aqueous HCl and allowed to stabilize at this pH. Separately, the pH of a freshly prepared 2 M aqueous solution of hydroxylamine hydrochloride was also adjusted to 4 with HCl. An aliquot of this solution (ca. 3 mL) was then rapidly introduced to vigorously stirred pulp suspension (large molar excess of hydroxylamine hydroxhloride). The pH of the mixture was maintained at 4 by titration of HCl formed with a 0.1 N NaOH solution using a Brinkmann pH STAT 718 Titrino. The titration was continued until no further reduction in pH of the mixture could be detected (ca. 1 h). Aldehyde level was calculated based on the total consumption of NaOH using the following equation (6.1 mmole/100 g cellulose pulp):

$$\text{mmole/100 g-CHO} = \frac{\text{mL of NaOH titrant} \times \text{N of NaOH}}{\text{pulp weight in g}} \times 100$$

The level of carboxylic acid formed during these treatments can be estimated from the amount of NaOH titrant consumed to maintain the pH of the reactions. This provides a direct indication of the additional carboxylic acid generated on the pulp and was calculated using the following equation:

$$\text{mmole/100 g-COOH} = \frac{\text{mL of NaOH titrant} \times \text{N of NaOH}}{\text{pulp weight in g}} \times 100$$

Alternatively, the total carboxyl content of the modified pulp was determined according to TAPPI 237 procedure for the determination of carboxyl content of pulp (8.0 mmole/100 g cellulose pulp).

b. Using a procedure similar to that described in Example 1a another batch softwood pulp was also modified to generate higher levels of aldehyde and carboxyl content by increasing the sodium hypochlorite treatment to 4% owp. Aldehyde and carboxyl content of this particular modified pulp was found to be 15.7 mmole/100 g and 17.7 mmole/100 g cellulose pulp respectively.

Example 2

Resilience and Absorbent Properties of Air Laid Pads

Samples of bleached southern softwood kraft pulp was oxidized according to Examples 1a and 1b. All modified and unmodified pulps were adjusted to a pH of 3.6 or 8.0 prior to sheet formation using dilute $H_2SO_4$ or NaOH, respectively. Air laid pads were then produced as described in the procedure section and tested for various properties in deionized water, saline, and synthetic urine.

TABLE 1

Absorbency Properties of Pads Containing Oxidized Pulps

| Sample | Carboxyl/ Aldehyde Content (mmole/100 g) | Water Absorbent Capacity (g/g) | Saline Absorbent Capacity (g/g) | Saline AUL (g/g) | Water Wicking Rate (cm/sec) | Saline Wicking Rate (cm/sec) | Synthetic Wicking Rate (cm/sec) |
|---|---|---|---|---|---|---|---|
| pH 3.6 | | | | | | | |
| Untreated | — | 12.3 | 11.4 | 5.17 | 0.34 | 0.35 | 0.31 |
| Treated | 8.0/6.1 | 14.3 | 13.7 | 5.60 | 0.59 | 0.41 | 0.39 |
| pH 8.0 | | | | | | | |
| Untreated | — | 12.7 | 11.2 | 4.86 | 0.34 | 0.38 | 0.30 |
| Treated | 8.0/6.1 | 13.8 | 12.6 | 5.82 | 0.60 | 0.52 | 0.52 |

The results recorded in Table 1, above demonstrate that the modified pulps of the present invention show improved wicking rate and absorbent capacity under both water and saline conditions as compared to untreated conventional pulps, particularly under loads commonly experienced in baby diapers.

TABLE 2

Resiliency Properties of Pads Containing Oxidized Pulps

| Sample | Carboxyl/Aldehyde Content (mmole/100 g) | Dry Resiliency @ 157 psi (mm) | Dry Resiliency @ 250 psi (mm) |
|---|---|---|---|
| pH 3.6 | | | |
| Untreated | — | 2.38 | 1.84 |
| Treated (via Example 1a) | 8.0/6.1 | 3.78 | 2.47 |
| Treated (via Example 1b) | 17.7/15.7 | 4.37 | 2.95 |
| pH 8.0 | | | |
| Untreated | — | 2.25 | 1.97 |
| Treated (via Example 1a) | 8.0/6.1 | 3.83 | 2.95 |
| Treated (via Example 1b) | 17.7/15.7 | 4.37 | 2.93 |

The data reported in Table 2 shows the improvement in structural integrity of the modified pulps of the present invention as measured by the substantial increase in dry resiliency as compared to the corresponding untreated pulp, even under high pressures of 250 psi.

Example 3

Southern bleached softwood kraft was oxidized according to the procedure described in Example 1 *a*, except that the reaction was run at a temperature of 10° C. at 5% consistency. Absorbent pads were made from the oxidized fibers according to the method described in the Procedure section.

Absorbent pads contained 10% SAP by weight of the total composite were also made from the pulp oxidized according to Example 1a. The hydrocolloid (SAP) used was a crosslinked sodium polyacrylate obtained from Stockhausen, Inc. AP70. The SAP was homogeneously blended with the fluff fibers and the composite pad was then pressed to a final density of 0.15 g/cm³ and weight of 650 g/m² for direct comparison.

The data demonstrating the integrity and saline absorbent properties of the modified pads as well as the wicking capacity are reported in Table 3.

TABLE 3

Properties of Modified Pads.

| Sample | Carboxyl/Aldehyde Content (mmole/100 g) | Saline Absorbent Capacity (g/g) | Saline Wicking Rate (cm/sec) | Saline Wicking Capacity (ml/sec) | Dry Resiliency at 157 psi (mm) | 10% SAP Saline Absorbent Capacity (g/g) |
|---|---|---|---|---|---|---|
| Untreated | — | 12.3 | 0.24 | 1.41 | 2.52 | 16.07 |
| Treated | 8.8/10.3 | 14.0 | 0.42 | 3.06 | 4.38 | 17.52 |

The data reported in Table 3 shows that the modified fluff pulp of this invention exhibits a surprising simultaneous increase in both the wicking rate and wicking capacity resulting in an overall improvement in fluid transport properties. Further, the data shows the improved absorbent capacity of the modified fluff pulp as well as an increased resiliency resulting in improved structural integrity as compared to the corresponding untreated fluff pulp.

Additionally, at the SAP level tested, Table 3 illustrates that a reduction in SAP content can be achieved when using the modified pads of this invention.

We claim:

1. A method of preparing modified fluffed pulp, the method comprising the steps of:
   oxidizing cellulose pulp in a suitable medium with an oxidant in the presence of a nitroxide radical mediator; and
   fluffing treated cellulose pulp, the treated cellulose pulp having from about 1 to about 50 mmole of aldehyde functionality per 100 grams of cellulose pulp;
   wherein the modified fluff pulp has an increase in wicking rate and wicking capacity compared to unmodified fluff pulp.

2. The method of claim 1 wherein the nitroxyl radical mediator is a di-tertiary alkyl nitroxyl radical having a formula of

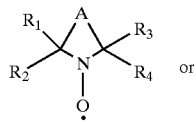

(I)

or

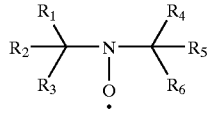

(II)

wherein A is a chain having two or three atoms; each atom is selected from the group consisting of carbon, nitrogen and oxygen; and the $R_1$–$R_6$ groups represent the same or different alkyl groups.

3. The method according to claim 2 further comprising at least one co-catalyst.

4. The seethed of claim 1 wherein the treated cellulose pulp has from about 1 to abut 20 mmole aldehyde groups per 100 grams of cellulose pulp.

5. The method according to claim 1 wherein the nitroxyl radical mediator or 4-acetamido TEMPO.

6. The method according to claim 1 wherein the nitroxyl radical mediator is an effective amount to mediate the oxidation.

7. The method of claim 6, wherein the amount of the nitroxyl radical mediator is from about 0.001 about 20% by weight based on the weight of cellulose pulp.

8. The method according to claim 1 wherein the oxidant is an alkali or alkaline-earth metal hypohalite having an oxidizing power of from about 0.05 to about 15.0 grams active chlorine per 100 grams of substrate.

9. The method according to claim 8 wherein the oxidant is sodium hypochlorite or sodium hypobromite.

10. The method according to claim 1 comprising the step of oxidizing the cellulose pulp in aqueous media with about 0.5% to about 20% sodium hypochlorite in the presence of from about 0.005% to about 5.0% 4-acetamido TEMPO, and up to about 5% sodium bromide, all percents by weight based on the weight of the cellulose pulp.

11. The method of claim 10 wherein the cellulose pulp is oxidized in the presence of about 1 to about 5% of sodium hypochlorite in the presence of 0.01% to about 0.1% 4-acetamido TEMPO; and from about 0.1% to about 2% sodium bromide, all percents by weight based on the weight of the cellulose pulp.

12. The method of claim 10 further comprising oxidizing the cellulose pulp in the presence of am about 0.005% to about 0.5% polyacrylamide.

13. The modified fluff pulp made according to the method of claim 12.

14. The modified fluff pulp made according to the method of claim 10.

15. The method of claim 1 wherein the treated cellulose pulp has an aldehyde to carboxylic acid functionality ratio of greater than 0.2 based on 100 g of cellulose pulp for each functionality.

16. The modified fluff pulp made according to the method of claim 1.

17. An absorbent article comprising the modified fluff pulp of claim 16.

18. The method according to claim 1 wherein the modified fluff pulp has an increase in structural integrity compared to an unmodified fluff pulp.

19. The method according to claim 1 wherein the modified fluff an increase in absorbent capacity compared to an unmodified fluff pulp.

20. The method according to claim 1 wherein the modified fluff pulp has an increase in odor reduction compared to an unmodified fluff pulp.

21. A method of preparing modified fluffed pulp, the method comprising the steps of:

oxidizing cellulose pulp in a suitable medium with an oxidant in the presence of a nitroxide radical mediator; and fluffing treated cellulose pulp, the treated cellulose pulp having from about 1 to about 50 mmole of aldehyde functionality per 100 grams of cellulose pulp;

wherein modified fluff pulp has an increase in structural integrity compared to an unmodified fluff pulp.

22. A method of preparing modified fluffed pulp, the method comprising the steps of:

oxidizing cellulose pulp in a suitable medium with an oxidant in the presence of a nitroxide radical mediator; and fluffing treated cellulose pulp, the treated cellulose pulp having from about 1 to about 50 mmole of aldehyde functionality per 100 grams of cellulose pulp;

wherein the modified fluff pulp has an increase in absorbent capacity compared to an unmodified fluff pulp.

23. A modified fluff pulp formed by oxidizing pulp in an aqueous medium with an oxidant in the presence of a nitroxide radical mediator and fluffing the pulp, the modified fluff pulp having an increase in wicking rate and winking capacity as compared to an unmodified fluff pulp.

24. An absorbent article comprising the modified fluff pulp of claim 23.

25. A modified fluff pulp formed by oxidizing pulp in an aqueous medium with an oxidant in the presence of a nitroxide radical mediator and fluffing the pulp, the modified fluff pulp having from about 1 to about 50 mmole of aldehyde functionality per 100 grams of cellulose pulp, the modified fluff pulp further having an increase in structure integrity as compared to an unmodified fluff pulp.

26. An absorbent article comprising the modified fluff pulp at claim 25.

* * * * *